(12) United States Patent
Parekh et al.

(10) Patent No.: US 10,772,635 B2
(45) Date of Patent: Sep. 15, 2020

(54) DEVICES AND METHOD FOR BLOOD VESSEL OCCLUSION

(71) Applicant: Front Line Medical Technologies Inc., London (CA)

(72) Inventors: Asha Parekh, London (CA); Adam Power, London (CA)

(73) Assignee: Front Line Medical Technologies Inc., London (CA)

( * ) Notice: Subject to any disclaimer, the term of this patent is extended or adjusted under 35 U.S.C. 154(b) by 122 days.

(21) Appl. No.: 16/197,862

(22) Filed: Nov. 21, 2018

(65) Prior Publication Data
US 2019/0192164 A1 Jun. 27, 2019

Related U.S. Application Data

(60) Provisional application No. 62/590,135, filed on Nov. 22, 2017.

(51) Int. Cl.
| | | |
|---|---|---|
| *A61B 17/12* | (2006.01) | |
| *A61M 25/10* | (2013.01) | |
| *A61M 5/00* | (2006.01) | |
| *A61B 17/00* | (2006.01) | |
| *A61B 90/00* | (2016.01) | |

(52) U.S. Cl.
CPC .... *A61B 17/12109* (2013.01); *A61B 17/1204* (2013.01); *A61B 17/12136* (2013.01); *A61M 5/00* (2013.01); *A61M 25/104* (2013.01); *A61M 25/1029* (2013.01); *A61B 17/12036* (2013.01); *A61B 2017/00526* (2013.01); *A61B 2017/1205* (2013.01); *A61B 2090/3966* (2016.02); *A61M 25/1002* (2013.01); *A61M 25/1018* (2013.01); *A61M 25/1034* (2013.01)

(58) Field of Classification Search
CPC ............... A61M 25/1018; A61M 5/00; A61M 25/1002; A61M 25/1029; A61M 25/1034; A61M 25/104; A61B 17/12036; A61B 17/1204; A61B 17/12109; A61B 17/12136; A61B 2017/00526; A61B 2017/1205; A61B 2090/3966
USPC ............................ 206/570, 571, 363–5, 477
See application file for complete search history.

(56) References Cited

U.S. PATENT DOCUMENTS

| | | | |
|---|---|---|---|
| 4,315,512 A | 2/1982 | Fogarty | |
| 4,821,722 A | 4/1989 | Miller | |
| 5,087,246 A | 2/1992 | Smith | |
| 5,135,494 A | 8/1992 | Engelson | |

(Continued)

FOREIGN PATENT DOCUMENTS

| | | |
|---|---|---|
| WO | WO9213589 A1 | 8/1992 |
| WO | WO9219311 | 11/1992 |

(Continued)

OTHER PUBLICATIONS

Jun. 3, 2019 PCT Search Report (Serial No. PCT/US18/62228).

*Primary Examiner* — Jocelin C Tanner
(74) *Attorney, Agent, or Firm* — Tysver Beck Evans

(57) ABSTRACT

An occlusion assembly and its uses in a REBOA procedure is disclosed. The occlusion assembly includes a single elongate shaft having an inflatable balloon, a proximal neck portion, a distal neck portion. The shaft defines a single lumen through which a wire is positioned for support of the shaft and through which an inflation fluid is also passed to inflate the balloon.

3 Claims, 11 Drawing Sheets

(56) References Cited

U.S. PATENT DOCUMENTS

| | | | |
|---|---|---|---|
| 5,318,587 A | | 6/1994 | Davey |
| 5,441,484 A | | 8/1995 | Atkinson |
| 7,261,205 B2 | * | 8/2007 | Cervantes ............. A61F 2/0095 <br> 206/363 |
| 7,331,463 B2 | * | 2/2008 | Hickey .................. A61B 50/30 <br> 206/438 |
| 2012/0296313 A1 | * | 11/2012 | Andreacchi ....... A61M 25/0668 <br> 604/509 |
| 2013/0178711 A1 | * | 7/2013 | Avneri .............. A61M 25/0023 <br> 600/208 |
| 2013/0225997 A1 | | 8/2013 | Dillard et al. |

FOREIGN PATENT DOCUMENTS

| | | |
|---|---|---|
| WO | WO9630074 | 10/1996 |
| WO | WO0069502 | 11/2000 |
| WO | WO09009472 | 1/2009 |

* cited by examiner

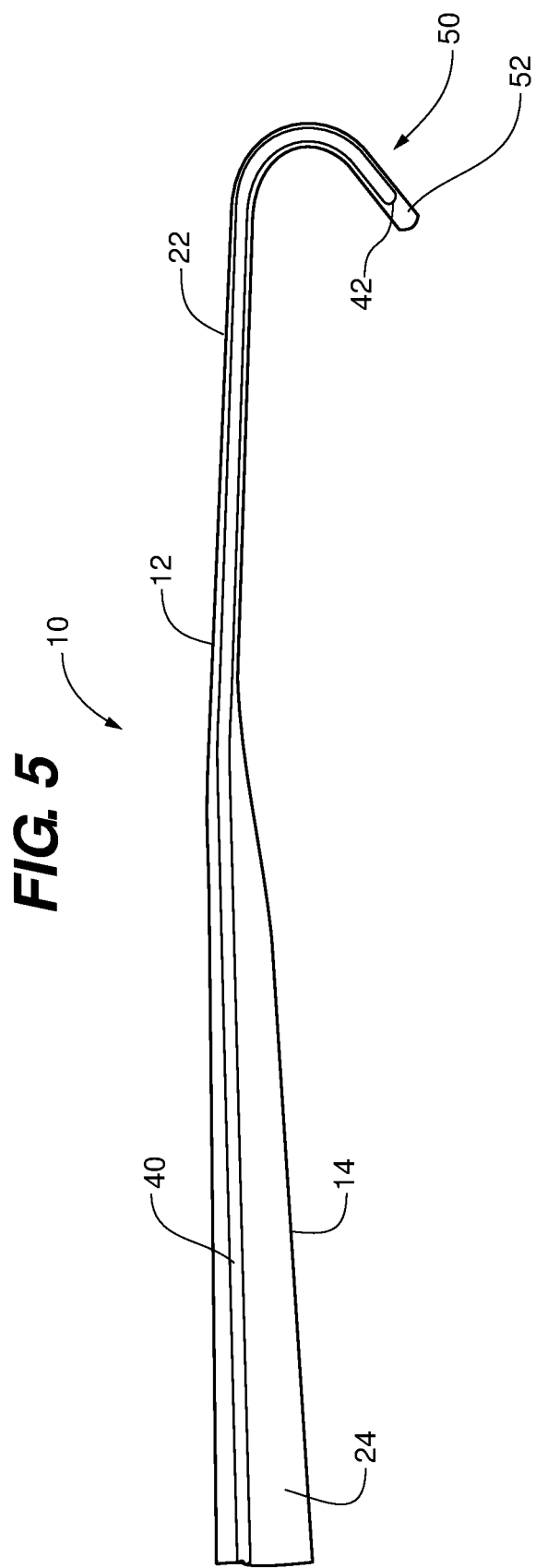

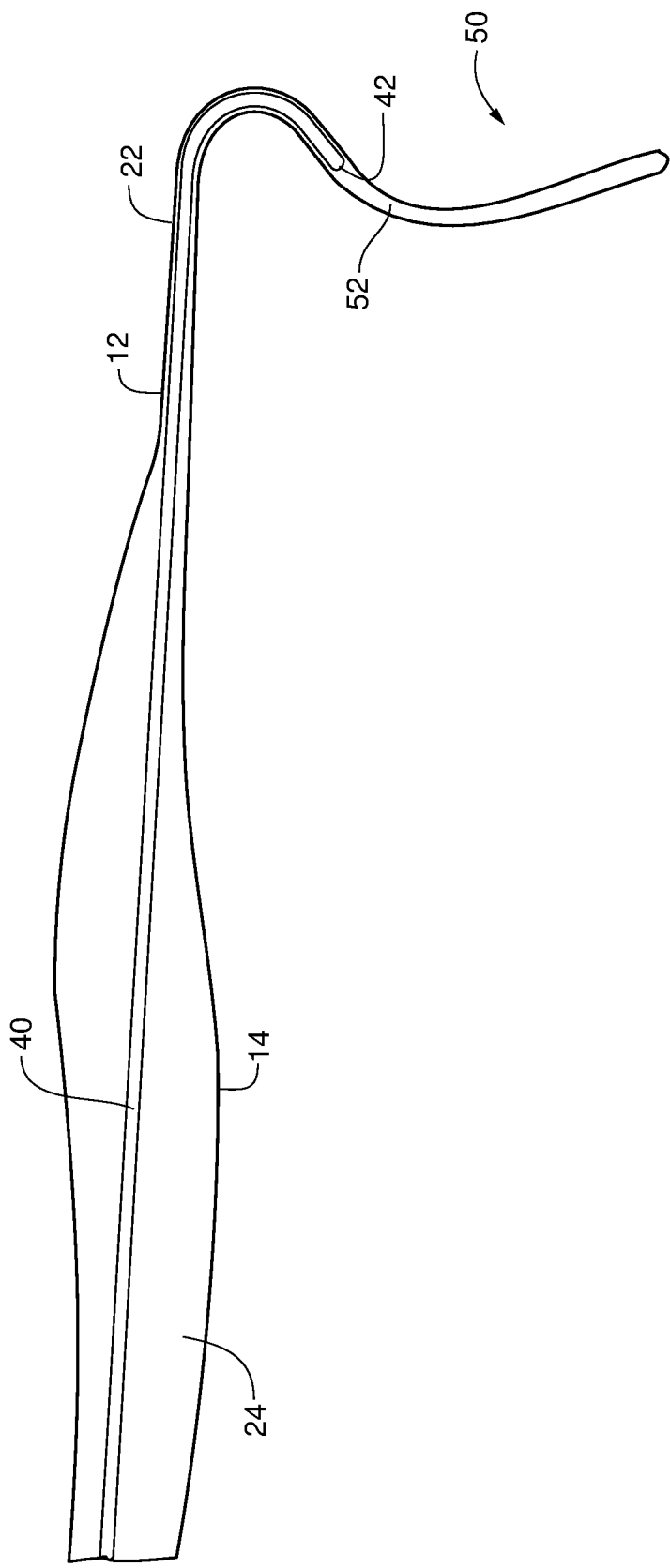

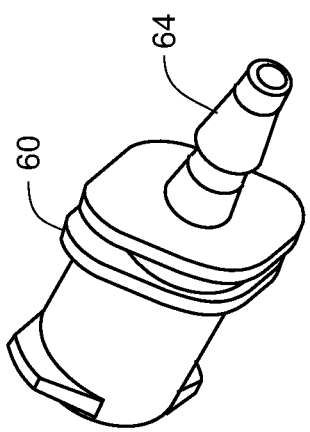
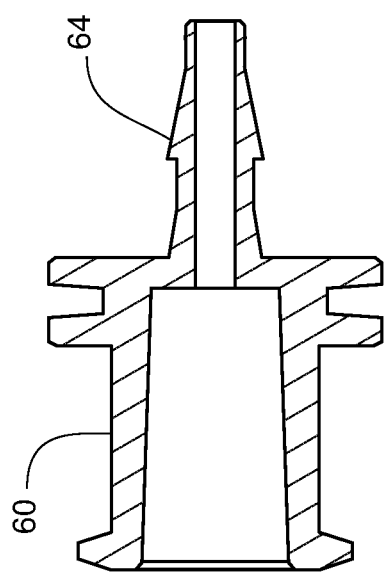
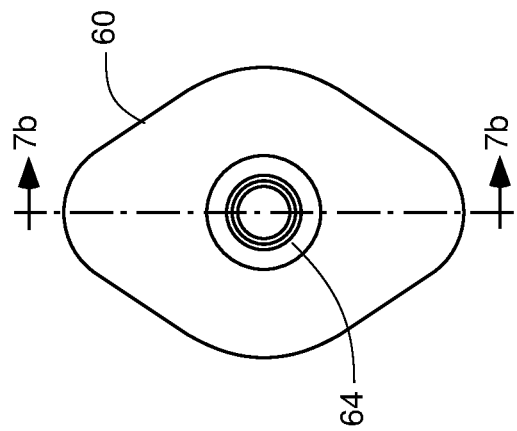

DEVICES AND METHOD FOR BLOOD VESSEL OCCLUSION

FIELD OF THE INVENTION

The present disclosure generally relates to the field of catheter assemblies and other devices for the temporary occlusion of a blood vessel. More specifically, the disclosure relates to Resuscitative Endovascular Balloon Occlusion of the Aorta (REBOA) via a unique occlusion assembly and method of employing the same.

BACKGROUND

Hemorrhage is the leading cause of death in military trauma and the second most leading cause of death in the civilian setting. Approximately 60% and 90% of these deaths occur before hospital admission in the civilian and military setting respectively, deeming them potentially preventable if an effective pre-hospital treatment were to exist. However, the on-site treatment options for non-compressible truncal hemorrhage are extremely limited in the pre-hospital setting. Thus, there exists a need for an on-site device/method for controlling excessive bleeding that does not require extensive surgical training or equipment. One option being developed to address this need are assemblies and medical techniques used for performing a REBOA procedure.

REBOA is an emerging technique used to support blood pressure and decrease hemorrhage in trauma. However, it requires expert surgical approaches and/or sophisticated equipment and therefore is largely not common practice. A retrospective analysis indicated that as many as 18% of modern combat casualties may benefit from REBOA treatment. This technique is less morbid than a resuscitative thoracotomy and may have a role in the hypotensive pre-arrest patient by increasing their blood pressure and decreasing hemorrhage before progression to arrest and the need for resuscitative thoracotomy.

REBOA is a new technique to military medicine, with the majority of data on REBOA coming from trauma and vascular surgeons with considerable endovascular experience, working in a civilian setting. Many of the pioneers of this technique espouse caution with its rapid adoption. Some authors have also cautioned against the widespread adoption of REBOA, fearing that use by less qualified practitioners may generate poorer outcomes before this technique has been adequately studied and its indications for use and required provider training has been defined. Most contributors to the American REBOA registries are trauma and vascular surgeons who have taken or are instructors on REBOA training courses.

Thus, there still exists a need for an on-site device/method to (temporarily) control non-compressible excessive bleeding that does not require extensive surgical training or equipment and that is easily portable, particularly for the military setting as well as other emergency situations.

One approach is to use a fairly standard angioplasty balloon device, which comprises a balloon and a balloon shaft with two inner lumens: one for filling the balloon and the other for tracking an endovascular wire. An angioplasty balloon device may further comprise two external ports or hubs for filling the balloon and for inserting an endovascular wire. A balloon may have certain compliances depending on the application. For example, compliant balloons are used for REBOA with a catheter that has a series of holes or ports that are in fluid communication with a "balloon-filling" inner lumen that allows the balloon to be filled.

Preferably, catheters used in REBOA techniques should have as low a profile as possible so as to minimize complications, particularly those that are associated with the risk of bleeding when accessing arteries. A lower profile catheter allows for easier insertion of the device since a smaller access hole in an artery will suffice. In turn, this may reduce or eliminate the need for large sheaths to guide entry. Furthermore, removal of the catheter may also reduce the risk of bleeding, since a smaller access hole also leads to reduced bleeding from the access site. A low profile catheter with the addition of an atraumatic tip offers other advantages including ease of use with minimal training and may also dispense with the need of using imaging, such as X-ray or US, for guiding the device to a target location for occlusion of an artery. Known REBOA balloons often require fluoroscopic guidance to make sure that the balloon is in place before inflation and occlusion of an artery.

For example, one known REBOA balloon is ER-RE-BOA™ Catheter from Prytime Medical™, which has a balloon attached to a catheter with two channels (one for inflating the balloon and the other for arterial blood pressure monitoring) extending from opposite ends of the balloon and uses a 7 French sheath. While a REBOA catheter of such a low profile is certainly an improvement over larger devices, even so, a need remains to provide a catheter suitable for use in REBOA procedures that has an even lower profile.

Embodiments of the present disclosure meet this need by providing a single lumen tube, rather than a more conventional catheter assembly, which by way of its more streamlined construction is capable of being inserted via a sheath as small as 4 French. Such an occlusion assembly is suitable for use in a variety of arterial locations that known devices are not (e.g. carotid artery, brachial artery, or radial artery access), may be utilized with or without the need of external visual imaging; and may as a consequence, be used in a greater range of potential patients (e.g. pediatric as well as adult) and in more diverse settings (e.g. rough field conditions as well as in-hospital settings) than known REBOA catheter systems. These and other benefits of the embodiments of the occlusion assembly disclosed herein will be made more apparent in the description below. It should be noted that the occlusion assembly can be used in a variety of applications in both the pre-hospital setting and in-hospital setting, such as but not limited to, postpartum hemorrhage, cardiac arrest, and any additional clinical scenarios where REBOA/blood vessel occlusion would be of benefit.

SUMMARY

In at least one embodiment, there is provided an occlusion assembly for occluding a blood vessel. The occlusion assembly has a lower profile than a conventional catheter, and comprises a single elongated balloon shaft comprising: an inflatable balloon portion having a distal and proximal end; a distal neck attached to the distal end of the inflatable balloon portion; and a proximal neck attached to the proximal end of the inflatable balloon portion; the elongated tube having an inner lumen expanding through at least the proximal neck and inflatable balloon portion, the inner lumen defining a flow channel for a fluid to inflate the inflatable balloon portion when the fluid is injected into the inner lumen from a proximal end of the elongated tube; and an endovascular wire inserted in the inner lumen having a first end terminating in the distal neck.

In another embodiment, the occlusion assembly comprises an elongated tube comprising: an inflatable first balloon portion; an inflatable second balloon portion; a distal neck attached to a distal end of the inflatable second balloon portion; a middle neck connecting a distal end of the inflatable first balloon portion to a proximal end of the inflatable second balloon portion; and a proximal neck attached to a proximal end of the first inflatable balloon portion; the elongated tube having an inner lumen expanding through at least the proximal neck, the inflatable first balloon portion, the middle neck, and the inflatable second balloon portion, the inner lumen defining a flow channel for a fluid to inflate the inflatable first and second balloon portion when the fluid is injected into the inner lumen from a proximal end of the elongated tube; and an endovascular wire inserted in the inner lumen having a first end terminating in the distal neck.

In another embodiment, there is provided a kit for occluding blood vessels, the kit comprising: a container; the occlusion assembly and wire as described above placed inside the container; and one or more connection pieces placed inside the container for attachment to the elongated tube, the one or more connection pieces having a first port for insertion of the wire and a second port for injection of the fluid.

Uses of the occlusion assemblies or kits as described above for REBOA is also provided.

In another embodiment, there is provided a method of occluding a blood vessel. The method comprises several steps. In one step a wire is inserted, or prepositioned, within a lumen of an elongated tube such as that of an occlusion member. The elongated tube comprises an inflatable balloon portion having a distal and proximal end, a distal neck portion attached to the distal end of the inflatable balloon portion, and a proximal neck portion attached to the proximal end of the inflatable balloon portion. An inner lumen extends through at least the proximal neck and inflatable balloon portion. The inner lumen containing the wire also acts as a flow channel for a fluid to inflate the inflatable balloon portion when the fluid is injected into the inner lumen from a proximal end of the elongated tube. An artery is punctured with a needle and a sheath is inserted, or an angiocatheter is used to puncture the artery and the needle is removed. The occlusion assembly are inserted into the artery through the sheath or angiocatheter to an appropriate length to reach a target location. Fluid is injected into the lumen from the proximal end of the elongated tube, which remains external of the artery, to inflate the inflatable balloon portion and occlude the artery at the target location.

These and other embodiments of the occlusion assembly disclosed herein are shown in the following images and the accompanying Detailed Description below.

BRIEF DESCRIPTION OF THE DRAWINGS

FIG. 5 is a close up view of a distal portion of the balloon and distal neck portion of the embodiment shown in FIGS. 2-4.

FIG. 6 is a close up view of a distal portion of the balloon and distal neck portion of the embodiment shown in FIGS. 2-4.

FIG. 7a is a perspective view of the luer lock shown in FIGS. 2-4.

FIG. 7b is a side sectional view of the luer lock shown in FIG. 7a.

FIG. 7c is a cross sectional longitudinal view of the luer lock shown in FIGS. 7a-7b.

DETAILED DESCRIPTION

Figure 1:
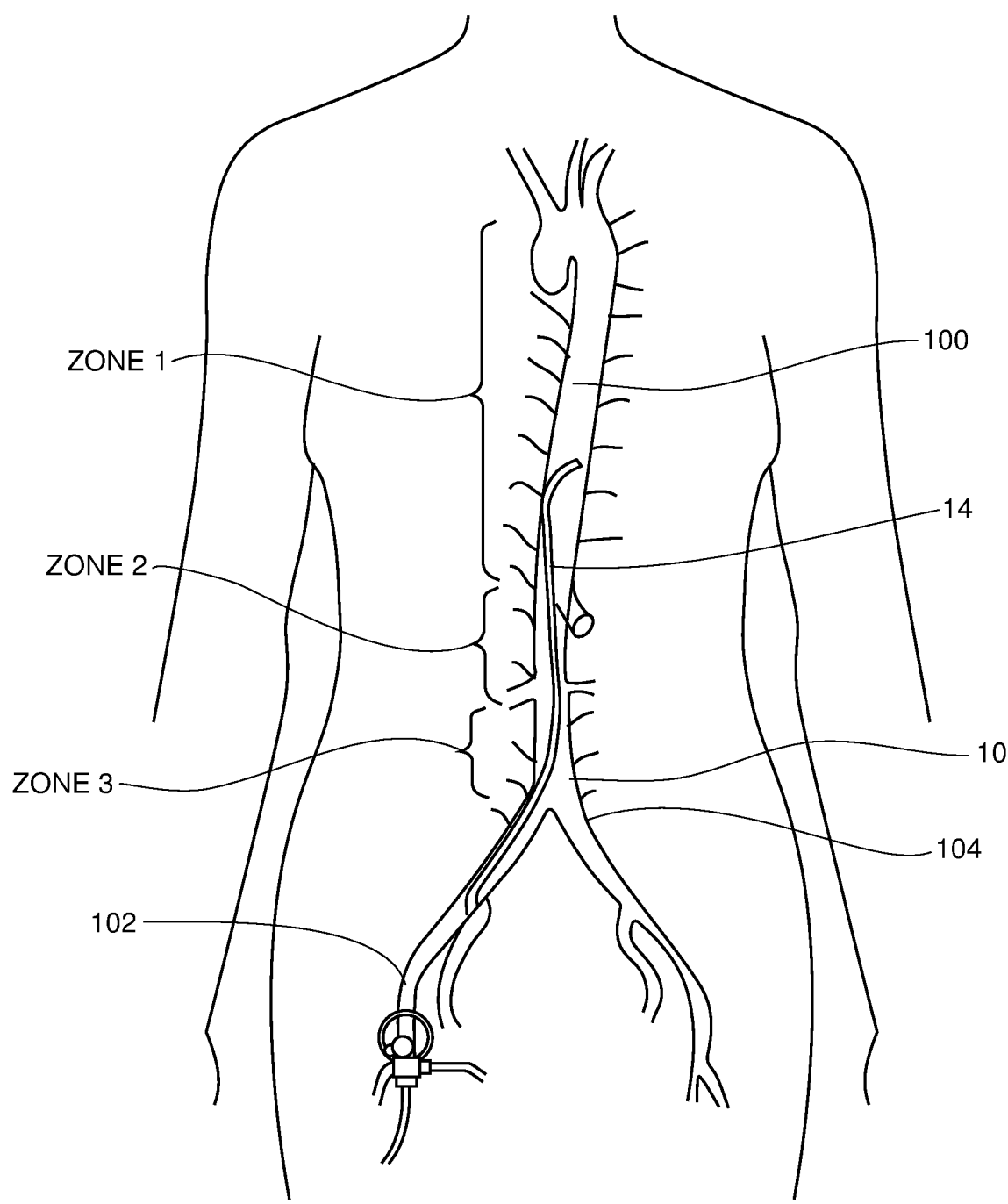
FIG. 1 is an illustration of a region of human anatomy wherein embodiments of the occlusion assembly are intended for use.

As indicated above, embodiments of the present invention are directed to an occlusion assembly 10 for use in REBOA procedures. An example of an occlusion assembly 10 of the present invention being advanced to a target site within a human aorta 100 is illustrated in FIG. 1. As is shown, the aorta 100 is divided into three zones or zones of deployment. As used herein, "zones" or "zones of deployment" refer to areas of intended aortic occlusion where the inflatable portion, or balloon portion 14, of the occlusion assembly 10 is to be deployed. Zone 1 extends from the origin of the left subclavian artery to the celiac artery and is a potential zone of occlusion. Zone 2 extends from the celiac artery to the lowest renal artery and is a no-occlusion zone. Zone 3 exists from the lowest renal artery to the aortic bifurcation. REBOA in this zone may provide particular utility for instances of pelvic and junctional femoral hemorrhage.

Though the occlusion assembly 10 may be inserted into the aorta using a variety of different arterial pathways, in the embodiment shown, the occlusion assembly 10 is inserted initially into the femoral artery 102, and then advanced into the aorta 100 beyond the aortic bifurcation 104. The occlusion assembly 10 is then advanced so as to position the balloon portion 14 into a desired deployment site within zone 1 or zone 3 where the balloon portion 14 is inflated so as to occlude the aorta.

Figure 2:
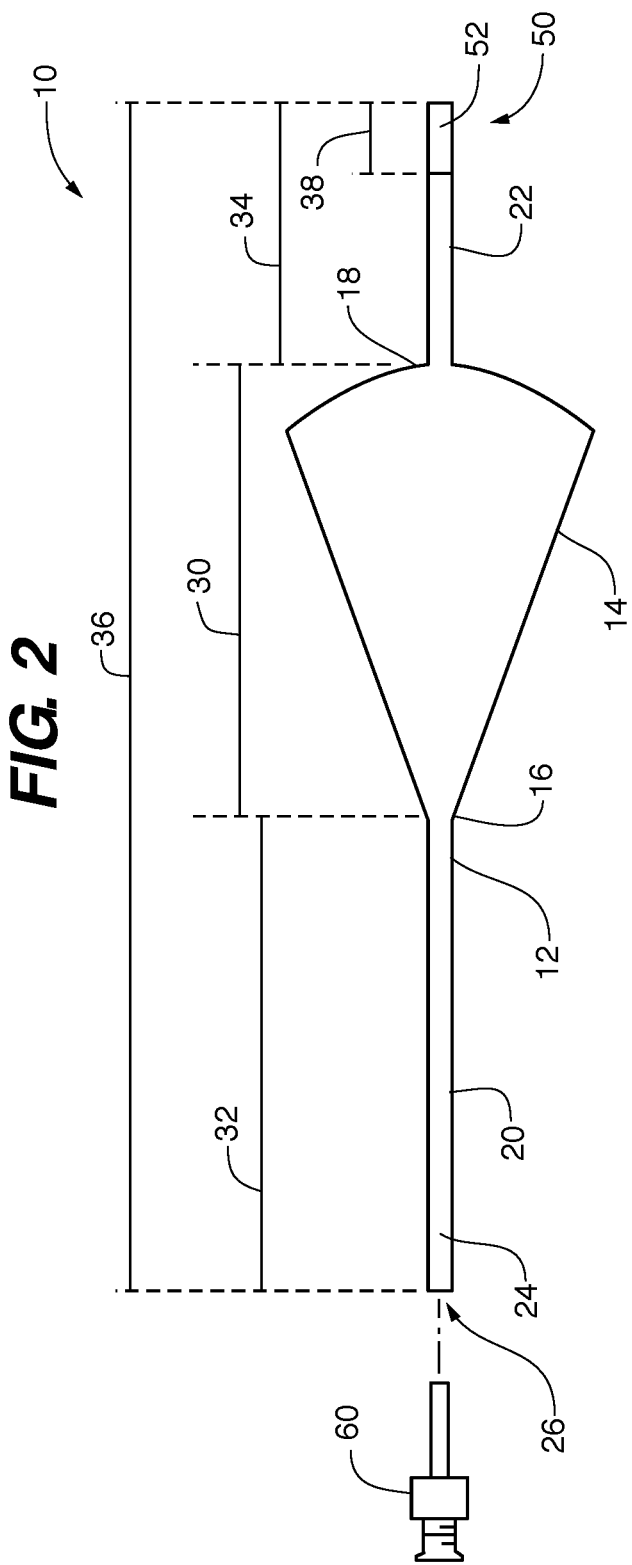
FIG. 2 is a side sectional view of an embodiment of the occlusion assembly showing the balloon shaft and luer lock.

Turning to FIG. 2, an embodiment of an occlusion assembly 10 is shown in more detail. The occlusion assembly 10 is comprised of an elongated balloon shaft 12 which includes an inflatable balloon portion 14 having a proximal end 16 and a distal end 18. A hollow proximal neck portion 20 of the shaft 12 extends proximally from the proximal end 16 of the balloon portion 14. A hollow distal neck portion 22 extends distally from the distal end 18 of the balloon portion 14. The balloon portion 14, proximal neck portion 20 and distal neck portion 22 are all in fluid communication with each other and define a common interior or lumen 24 through which the balloon portion 14 may be inflated and an endovascular wire may be positioned.

In a preferred embodiment, the distal and proximal neck portions 20 and 22, as well as the inflatable balloon portion 14 are provided or manufactured as a single integral structure (i.e. a balloon shaft 12). This single shaft of material is made by blow moulding or by other moulding processes such as extrusion moulding (or a combination of such processes). The single continuous lumen 24 extends the length of this balloon shaft 12. In one embodiment, the balloon shaft 12 is made with urethane, such as a low durometer urethane.

In some embodiments, the distal and proximal neck portions 22 and 20 have a thicker wall or layer of urethane than the balloon portion 14, such that when a fluid is injected into the lumen, the balloon portion 14 preferentially fills with the fluid thereby inflating the balloon portion. In some embodiments, the less compliant distal and proximal neck portions 20 and 22 do not inflate, or do so minimally (i.e. to a far less degree than the balloon portion 14, if at all, such that the distal and proximal neck portions do not in any state act to occlude the vessel where the balloon portion 14 is deployed) when the balloon portion 14 inflates.

The single integral balloon shaft 12 can also be manufactured by a combination of blow-moulding and buttwelding an appropriately sized extrusion tubing in order to get longer lengths than only blow-moulding would accomplish with traditional moulding processes.

Further advantages from having a single integral balloon shaft 12 include, for example, simpler and cheaper manufacturing as well as an even smaller profile. Most preferred embodiments of the occlusion assembly having a single integral structure can be used with sheaths of 5 French or less, for example a 4 French sheath. In contrast for example, ER-REBOA™ brand catheter requires a 7 French sheath. Furthermore, as the profile of a typical multi-channel angioplasty balloon device lowers, the smaller the flow channel becomes for the fluid. Eventually, the flow channel of the catheter is so small that only gases can flow through. The occlusion assembly 10 according to the present disclosure allows for a lumen 24 that provides a reasonable flow channel even with the wire 40 in place, such that fluids can be used to inflate the balloon at lower profiles than other REBOA devices. If a catheter is used instead to provide the stiffness to allow placement of the device and occlusion of the aorta, such as with the ER-REBOA™ Catheter from Prytime Medical™, then the catheter limits the profile of the device (7 French) and therefore the inner lumen for flow. If a catheter and wire are used to provide the stiffness, such as with the Coda Balloon™ from Cook Medical, then both the catheter and wire limit the profile of the device (12 French) and therefore the inner lumen of flow. The present invention allows for a very thin occlusion assembly (minimal stiffness) with a single integral lumen and a stiff low profile wire that allows for maximal flow of fluid at the lowest profile to achieve aortic occlusion.

In some embodiments, the balloon portion 14 is inflatable to 3-4 cm in diameter to correspond with typical aortic sizes of 2-3 cm. In some cases, the balloon is manufactured to inflate up to a predetermined diameter (usually a semi-compliant or non-compliant balloon). However, when using a compliant balloon with the preferred embodiment, the balloon is often overinflated to provide occlusion of the blood vessel. In one embodiment, the balloon measures about 6 cm in length but can be as short as 1-2 cm. The sizes and lengths of the balloon are not limited by the embodiments described herein, but may be larger or smaller based on intended use or need. Example materials for manufacturing the balloon include, but are not limited to PET, Nylon, Polyurethane, or other thermoplastic elastomers. One preferred material is a low durometer or soft urethane.

In some embodiments, the distal neck portion 22 is about 4 cm to about 15 cm in length, preferably 10 cm-15 cm in length, most preferably about 15 cm in length. This allows the leading edge of the wire 40/catheter distal portion 22 to safely guide the balloon portion 14 to the appropriate position. In some embodiments, the proximal neck portion 20 is about 10 cm-40 cm in length, most preferably about 20 cm for a zone-3 occlusion assembly or 40 cm for a zone-1 occlusion assembly. The lengths of the distal and proximal neck portions are not limited by the embodiments described herein, but may be longer or shorter based on intended target location or occlusion site.

The length of the distal neck portion 22 and proximal neck portion 20 of the balloon shaft 12, and the balloon portion 14, also depends on the distance between an access point and a target location. For example, from a femoral access point to the aortic bifurcation this distance is about 20-25 cm, and correspondingly an occlusion assembly 10 should allow the balloon portion 14 to be positioned at this distance from the access point for zone 3 deployment for example. In an adult it is approximately 20 cm from the femoral access point to the aortic bifurcation (the balloon is positioned above this) and 30 cm to the renal arteries (the balloon is positioned below this) for zone 3 deployment. To achieve this positioning, the proximal neck portion 20 and balloon portion 14 measures 20 cm deflated, but when inflated, it grows in length, up to about 25 cm. In one embodiment of the occlusion assembly for zone 3 deployment, the total length of the proximal neck and inflated balloon is about 26 cm. For example, the proximal neck is 20 cm and the balloon portion is also 26 cm. Other combinations are also possible to achieve a total length of 20-30 cm (deflated-inflated, respectively) for zone 3 deployment.

In at least one embodiment, the occlusion assembly 10 is adapted for zone 3 deployment only. In other embodiments, the device is adapted for zone 1 deployment, zone 2 deployment, zone 3 deployment, or combinations thereof. For overall safety, occluding in zone 3 is much safer than occluding in zone 1 for novice users. The length can be changed to comply with other zones or other access points. For example, zone 1 is approximately 20-25 cm from the carotid access point. In the 20-25 cm effective length example described above, the device can also be deployed from the carotid artery to obtain zone 1 deployment. Zone 2 deployment is approximately 30-40 cm and zone 1 is approximately 40-60 cm from the femoral access point. Accordingly, in one embodiment of the occlusion assembly for zone 2 deployment the proximal neck and balloon together measures about 30-40 cm (deflated-inflated); while in another embodiment for zone 1 deployment the proximal neck and balloon together measures about 40-60 cm (deflated-inflated).

Regarding the balloon portion 14, example shapes of the balloon include, but are not limited to round, spherical, tubular, conical, or "ice-cream cone" shaped, or any other shape based on target location and desired use. In one embodiment, an example of which is shown in FIG. 2, the balloon portion 14 is "ice-cream cone" shaped measuring 6 cm in length 30, with a proximal neck portion 20 having a 20 cm length 32 and a distal neck region 22 having a 15 cm length 34, to provide a total balloon shaft 12 length 36 of 41 cm. The advantage of the ice cream cone configuration includes, for example, that it stays in place much better than spherical balloons putting more pressure on the vessel wall at the superior edge of the balloon than the inferior edge. The other advantage of this shape, combined with the fact that the balloon is not fixed to the wire, is that the balloon portion can move forward or backward depending on the narrowing of the blood vessel. For example, if the balloon is being inflated in the iliac artery mistakenly for a zone 3 deployment, the shape of the balloon allows the balloon portion to move upwards to aortic bifurcation rather than staying fixed in the iliac artery. Therefore there is less risk of vessel rupture with this shape. Another advantage of this shape allows the balloon to sit on the aortic bifurcation and be fixed in position, preventing the balloon from migrating, important especially during patient transport. As used herein, "ice-cream cone" shaped refers to a shape having a generally tapered conical shape attached by the conical base to the plane surface of a hemisphere.

As previously mentioned, the common lumen 24 of the shaft 12 extends through the proximal neck portion 20, the balloon portion 14 and the distal neck portion 22. While this space is utilized as an inflation lumen through which inflation fluid may be transmitted from the open end 26 of the proximal neck portion 22 and into the balloon portion 14, the lumen is also configured to receive a wire 40 therein.

Figure 3:
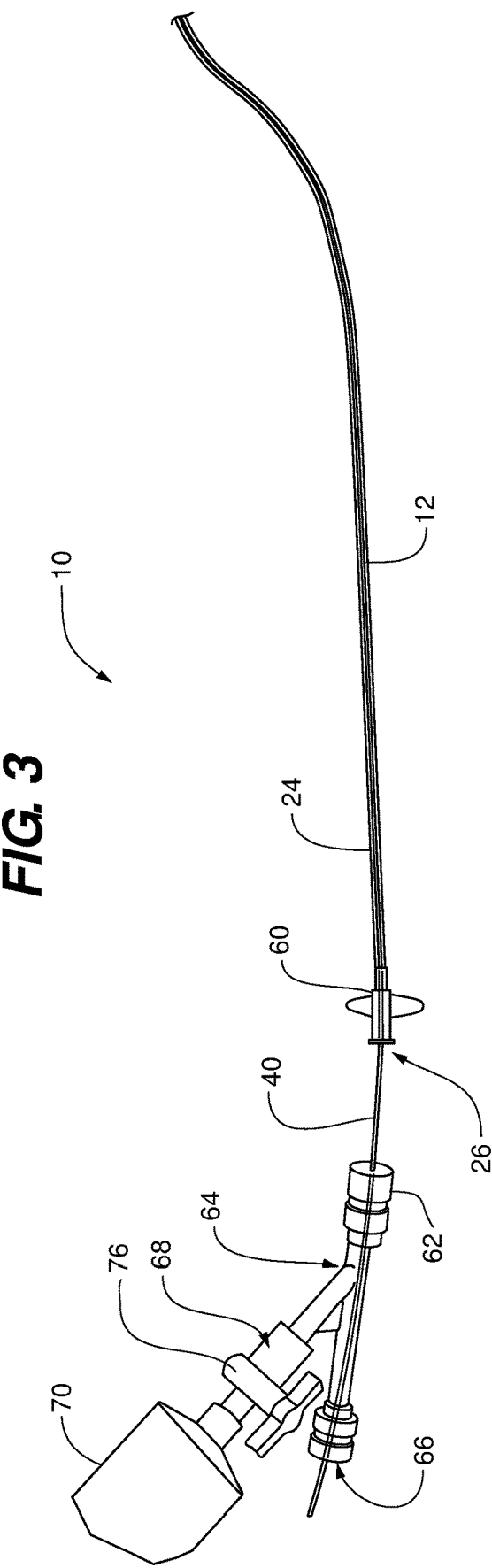
FIG. 3 Is a side perspective view of an embodiment of the occlusion assembly shown in FIG. 2 wherein a wire is shown passing through the shaft and lock and before connection with the handle assembly.

The wire 40 is inserted through the lumen 24 from the open end 26, such as in the manner shown in FIG. 3. While the wire 40 may be inserted into the lumen 24 and advanced to the distal end region 50 (see FIG. 5 for example) of the shaft 12, in at least one embodiment the wire 40 is pre-positioned within the lumen 24, having no part of the wire exposed or exiting from either the proximal end or distal end of the shaft 12. This minimizes the need of a user to manipulate the various components of the assembly and ensures a quicker, safer and more efficient deployment. The wire can also freely move within the balloon in the preferred embodiment, or can be fixed or bonded at the proximal neck end, distal neck end, or both ends.

As will be recognized by one of ordinary skill, an occlusion assembly 10 such as is shown in FIG. 2 avoids the need of providing a multi-layer or multi-channel catheter having a dedicated inflation lumen and dedicated guidewire lumen. By having a single lumen 24 performing the 'double duty' of both the wire lumen and inflation lumen provides an occlusion assembly 10 with reduced structure and thus reduced profile. Likewise, this configuration requires less materials from which the assembly is constructed and reduced manufacturing costs as well. As a result, the occlusion assembly 10 can be more inexpensively produced while providing a smaller package, which is ideal, for example in military applications.

Turning first to the functionality of the lumen 24 in containing a wire 40, in some embodiments, the wire 40 extends from the proximal neck portion 20 and into the balloon portion 14. In a preferred embodiment, the wire extends from the proximal neck portion 20, through the balloon portion 14, and into the distal neck portion 22, such as in the manner shown in FIG. 4.

In some embodiments, the wire 40 extends beyond the length of one or both of the distal and proximal neck portions. Where the wire 40 extends distally beyond the distal neck portion 22, the wire 40 requires bonding to the distal neck portion 22 so as to provide a leak-proof system. In a preferred embodiment, the wire 40 terminates at the distal end region or tip 50 of the distal neck portion 22, such as in the manner shown in FIG. 5.

In one embodiment, the tip 50 of the distal neck portion 22 is a blind ended segment. The tip 50 is bonded with an adhesive so that the wire 40 doesn't extend beyond the distal neck. Various methods of closing the tip 50 are available, including sealing off the distal neck portion 22 during the balloon manufacturing process. In at least one embodiment, an example of which is shown in FIG. 2, the distal end region 50 of the distal neck portion 22 includes a plug or bonded region 52 of 1-3 cm in length 38, against which the terminal end 42 of the wire 40 abuts and pushes against during advancement of the occlusion assembly 10 to a target site. The plug or bonded region 52 can have an appropriate length that enables easier placement of the occlusion assembly 10 into a sheath or angiocatheter, without the use of a straightener for the distal neck portion 22. The distal neck portion 22 can also take various configurations, such as a curved J-shape, to further maintain an atraumatic distal end.

In some embodiments, examples of which are shown in FIGS. 5 and 6, the tip 50 is shaped into various configurations such as J-tip, p-tip, straight, or angled to help ensure atraumatic passage of the balloon shaft 12 through the anatomy.

In a preferred embodiment, the wire 40 is an endovascular wire and adapted to thread through the balloon portion 14 and neck portions 20 and 22 to provide the stiffness or support necessary for guiding the occlusion assembly 10 and the balloon portion 14 into position within an artery, and keep it there; in particular, as the balloon portion 14 experiences blood flow that pushes against the balloon portion 14 as it is directed toward the target location in an artery. For example, when the balloon portion 14 is deployed retrograde from the femoral artery and blood is pushing the balloon portion 14 forward from the heart. Accordingly, the wire 40 is adapted to allow the balloon portion 14 to be placed into position, and to allow the balloon portion 14 to stay in position without slipping.

As mentioned elsewhere, in a preferred embodiment the wire 40 is prepositioned within the lumen 24, extending along the length of the shaft 12 from near the proximal end of the shaft 12 and terminating at a point adjacent the distal tip 50 (see FIG. 5).

Wire 40 may be any type of guide wire. Guide wires come in two basic configurations: solid steel or nitinol core wires and solid core wire wrapped in a smaller wire coil or braid. Coiled or braided wires offer a large amount of flexibility, pushability and kink resistance. One example wire is a guide wire from Boston Scientific™ which use a nitinol tube with micro-cut slots instead of braided wire to improve torque control. Nitinol wire, used by itself or braided with stainless steel, helps increase flexibility and allows the wire to spring back into shape after navigating a tortuous vessel segment. Guide wires often have a floppy tip and a stiff body to enable easy tip navigation, with good pushability offered by the stiffer section of the wire. Some wires are coated with a polymer, such as silicone or polytetrafluoroethylene (PTFE), to increase lubricity. Hydrophilic coatings reduce friction during deployment and for easier movement in tortuous vessels. The wires are sometimes hard to see on fluoroscopic X-ray imaging, so radiopaque markers are commonly used to improve visibility. These include gold marker bands or the addition of a platinum wire. The tips 42 of the wires come in various configurations, including a "J" curve, a variety of angles or straight tips to help navigate various vessel anatomies (see FIGS. 5-6 for example). Wire diameters are measured in thousandths of an inch, usually between 0.014 and 0.038 inches. Lengths are measured in centimeters, ranging from 80 to 450 cm.

In one embodiment, the wire 40 is 0.035-inch diameter; having length of at least 24 cm; and is a stiff stainless steel wire with hydrophilic coating. The Cook Medical™ amplatzer wire or lunderquist wire are examples which can be used with the balloon shaft 12. In some embodiments, the endovascular wire has a diameter of 0.035, 0.025, 0.018, or 0.014 inch. Accordingly, the lumen 24 of the balloon portion 14 and proximal and distal neck portions 20 and 22, have a diameter that is slightly greater than the diameter of the wire 40 to provide room around the wire 40 for filling of the balloon portion 14 with a fluid (liquid or gas). In one embodiment, wire 40 has a 0.035-inch diameter, while the outer diameters of the distal and proximal neck portions 20 and 22 are 55 mils (1.39 mm); and the proximal and distal neck portions 20 and 22 as well as balloon portion 14 will fit into and through a 4 Fr sheath or 14-gauge angiocatheter.

Typically, and especially for REBOA procedures wherein the deployment zone is known or the occlusion assembly 10 is pre-configured for such zone-specific use, the wire 40 is selected to have a length corresponding to the length necessary to position the balloon portion 14 in the desired zone. In such embodiments the wire 40 may be provided with markings or other indicia to indicate position within the body (e.g. gold or other materials to provide visual confirmation of position under fluoroscopic review, etc.) and/or have length markings visible through the proximal neck portion 20 to provide an easily viewed indicator of shaft depth when the shaft is advanced into the position.

One of the advantages of having a wire 40 provide the support and guidance of the balloon portion 14 is that the user can also choose the stiffness of the device (stiffness of the balloon) and shape/flexibility of the wire tip 42. The stiffness ultimately holds the balloon portion 14 in place during deployment. Conversely, the tip 42 allows the atraumatic introduction of the device and can be of various shapes, for example, straight floppy and j-tip floppy.

For example, a wire may have a floppy tip portion inserted into the distal neck portion 22 of the balloon shaft 12, and accordingly the distal neck portion 22 is sized or has sufficient length to accommodate the floppy tip portion 42 of the wire 40. The floppy tip of a wire is typically about 4-15 cm in length depending on the wire, and accordingly the distal neck is slightly longer than 4-15 cm. The sizes or lengths of the distal neck are not limited by the embodiments described herein, but may be size accordingly depending on the type of wire used.

The inserted wire 40 allows for the fact that you can adjust the stiffness of the device by switching to a different wire. Other advantages include the ability to change the leading edge because the wire 40 is the leading edge (J-tip, straight, angled); also, the wire 40 is protected by the urethane so is less traumatic travelling through the blood vessel. Also, there is less of the device hanging out of the patient meaning less chance to dislodge; reduced parts so less chance of leakage of fluid and losing balloon occlusion; less balloon rupture because the balloon is able to mould to the vessel better and move forward or backward to adjust to the blood vessel. Particularly, there is less leakage since the balloon portion 14 is not separately attached to a catheter shaft or similar housing. The wire 40 may also take other shapes, such as a double curve or extended curve as used in the Cook Medical Lunderquist wire, that enables much more variability in the shape of the overall occlusion assembly 10. The double curve is especially useful if the occlusion assembly 10 is inserted from an upper extremity access approach and has to curve into the descending thoracic aorta to provide aortic occlusion.

Figure 4:
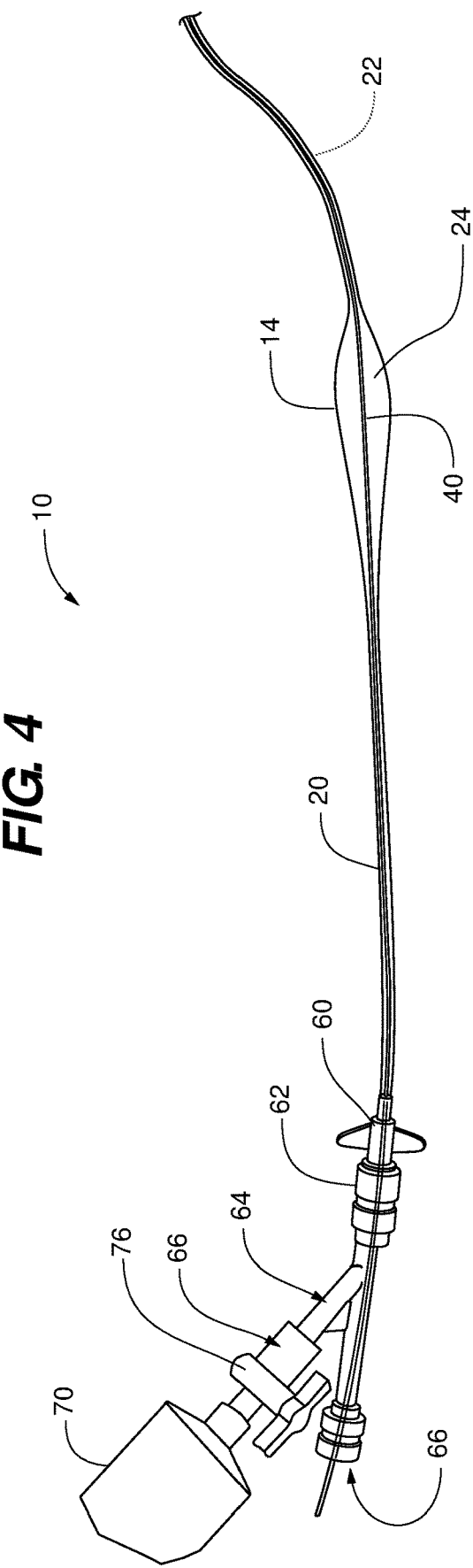
FIG. 4 is a side perspective view of the assembled occlusion assembly shown in FIGS. 2-3.

Returning to the example assemblies 10 shown in FIGS. 2-4, it is shown that in some embodiments the occlusion assembly 10 employs a luer lock or lug 60 for attaching the proximal neck portion 20 of the balloon shaft 12 to a connection piece such as a tuohy borst valve assembly 62. A detailed example luer lock or lug 60 is shown in FIG. 7a-7c. Examples of connection pieces 62 include, but are not limited to, valves, stop-cocks, joiners, extension tubing, or other connection pieces based on desired function or use.

Preferably, the connection piece 62 provides the device with one or more ports or hubs. In one embodiment, the luer lock 60 is bonded to the open end 26 of the proximal neck portion 22 with an adhesive. Various adhesives may be used, for example, medical adhesives such as cyanoacrylate or thermal bonding adhesives. In some embodiments, the luer lock 60 can also have a tapered tip 64 which mechanically engages and is received into the lumen 24 at the open end 26 of the proximal neck portion 20, and retained within the balloon shaft 12 by frictional engagement therewith. In one example, the luer lock 60 is a female luer lug to classic barb.

In some embodiments, the occlusion assembly 10 comprises two ports or hubs in a Y-adapter or handle assembly 64, a first port 66 receives and allows passage of the wire 40 into the lumen 24 and the second port 68 receives inflation fluid into the lumen 24 to inflate the balloon portion 14. The first "wire port" 66 must be linearly aligned with a longitudinal axis of the shaft 12, in order to receive the wire without causing the wire to become bent while inserting. The second "fluid inflation port" 68 may be angled relative to the longitudinal axis of the proximal and distal necks and the balloon.

One example of a two-port handle assembly 64 is show in FIGS. 3 and 4, which includes a tuohy-borst valve attachment 62 that is attached to the lock 60. In this embodiment, the adapter 64 provides a port 68 for fluid connection to a syringe 70 for inflating the balloon portion 14, and a port 66 for the wire 40. Accordingly, the wire must be long enough to extend through the proximal and distal neck portions 20 and 22 and the balloon portion 14, as well as through the handle assembly 64. In some embodiments the handle assembly 64, and/or the tuohy-borst valve attachment 62 may lock the wire 40 into a set position within the balloon shaft 12.

Figure 8:
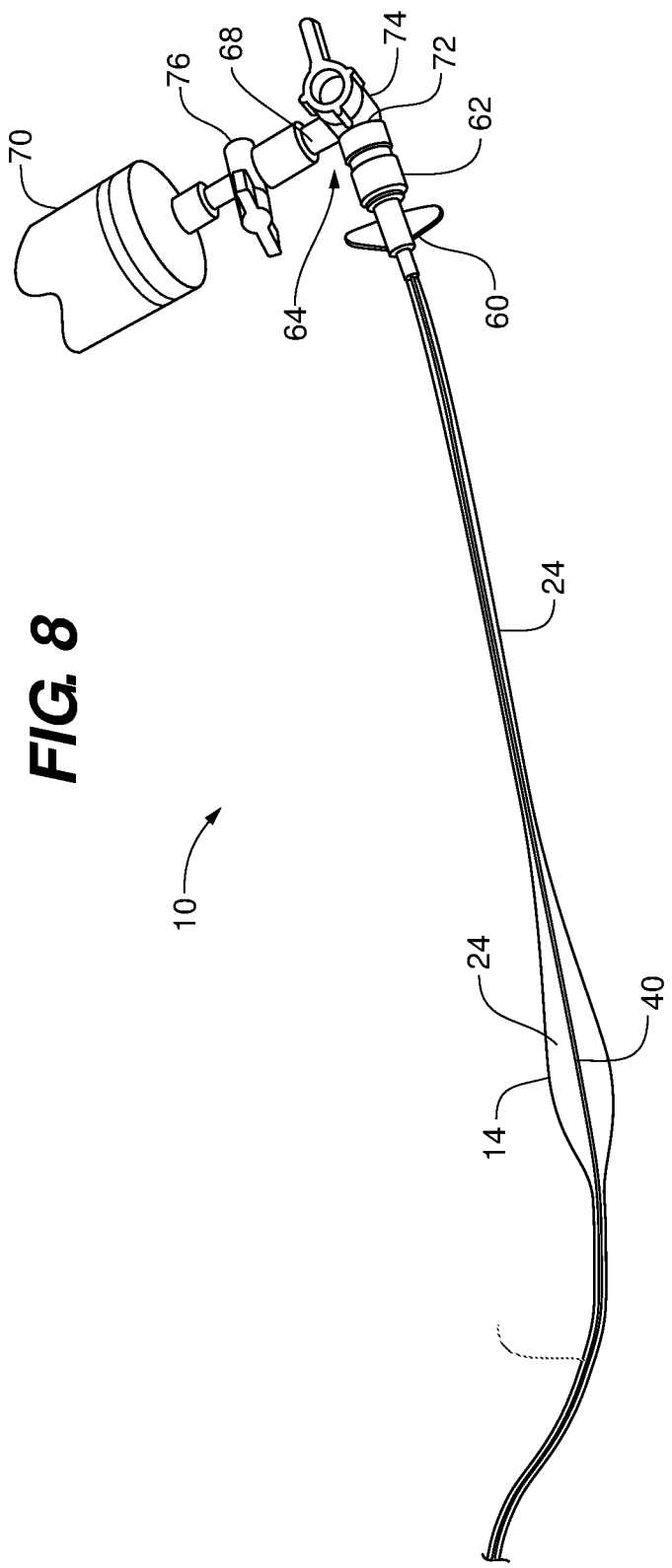
FIG. 8 is a perspective view of an embodiment of the occlusion assembly having an alternative handle assembly.

In some embodiments, an example of which is shown in FIG. 8, the handle assembly 64 includes only a single-port 72 wherein the wire 40 is kept inside or contained within the balloon shaft 12. In this embodiment, a three way stop-cock 74 is attached to the luer lock 60 to hold the wire 40 inside the balloon shaft 12. The three way stop-cock 74 has an inflation port 68 for fluid connection to a syringe 70, for inflation of the balloon portion 14 by filling the balloon with a fluid via lumen 24. In some embodiments, the fluid is a gas, a liquid, or air. Optionally, a second stop-cock 76, for example a two-way stop-cock, is attached between the inflation port 68 and syringe 70. The second stop-cock 76 allows the balloon to be "locked off" so that no gas/air/liquid could escape. Any series of stop-cocks, joiners, etc. can be used with this single-port occlusion assembly 10.

It is noteworthy that embodiments of the present occlusion assembly 10 wherein the wire 40 is contained entirely within the balloon shaft 12 and in the preferred embodiment is not fixed, are distinct from known angioplasty balloon devices, which have wires that extend beyond the balloon and catheter at the proximal end relative to the user and/or the distal end, such that device can be tracked over the wire.

Figure 9:
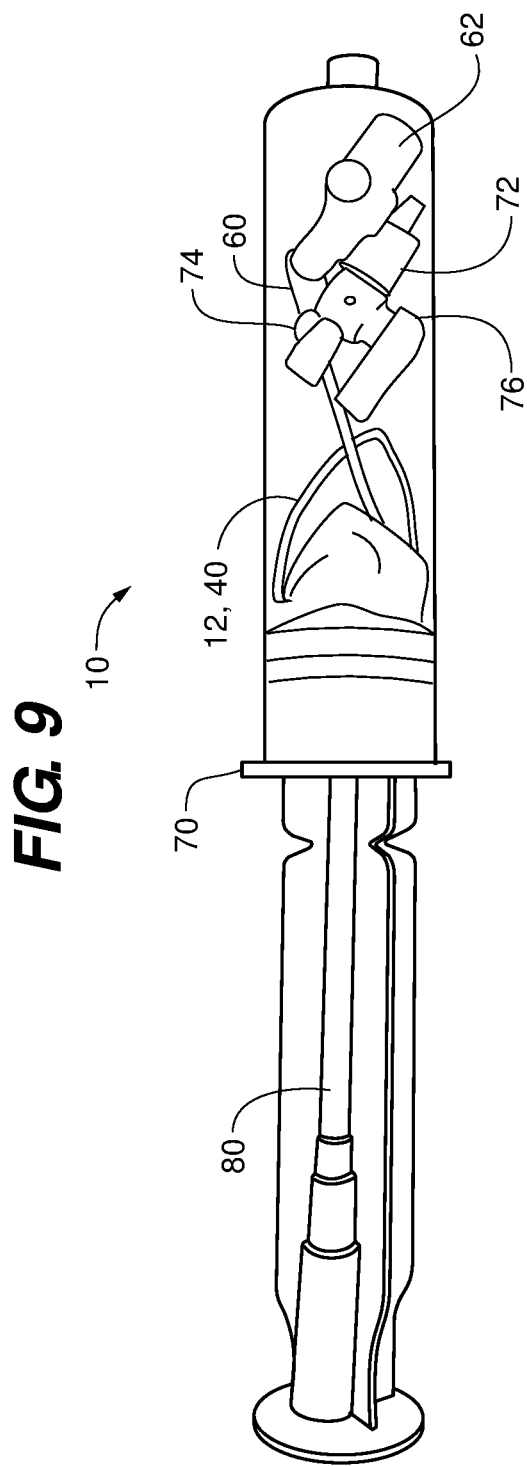
FIG. 9 is a perspective view of a syringe containing and including all of the components of the occlusion assembly shown in FIG. 8 and presented as a self-contained kit.

FIG. 9 shows an example packaging for an occlusion assembly 10 of the type discussed above and shown in FIG. 8. One advantage of embodiments of the occlusion assembly 10 as described above is the reduced number of components needed to perform the occlusion procedure. As such, the occlusion assembly 10 can be provided in a small package. This will be an advantage in multiple environments, especially in the military, where supplies must be small and light in weight. For example, the occlusion assembly 10 can be provided in a syringe 70, such as a 60-cc syringe. The wire 40, stop cock(s) 72 (76), balloon shaft 12, insertion needle 80 (angiocatheter, etc.) etc. can all fit within the confines of the barrel of a 60-cc syringe, either pre-assembled or to be assembled when used. In some embodiments, the syringe 70 and the syringe contents are sterilized, whereby the syringe acts as a sterilization compartment for keeping the occlusion assembly 10 sterilized.

Further embodiments of the occlusion assembly 10 comprise multiple balloons. For example, an occlusion assembly 10 can have a double balloon configuration; one balloon on the inside of the body and another on the outside of the body. The additional balloons can be of various shapes and sizes. The advantage of this is that the outside balloon can be a surrogate to how "filled" the inner balloon is. Novice users of REBOA often don't know how much to inflate the balloon and it often remains underfilled or can rupture a blood vessel or balloon if overfilled. Another advantage of this outer balloon is that it provides a quick reference that the fluid/air hasn't leaked out during transport of the patient. The double balloon can also be used in transferring air/gas/liquid from the outer to the inner balloon by collapsing the outer balloon, which simultaneously inflates the inner. The balloons do not have to have the same dimensions, and the outer balloon can be smaller so that it is more user-friendly. In one embodiment, the outer balloon does not start to inflate until an inner pressure has been reached, such as for example 100 mmHg, which would occlude the aorta in most individuals. The outer balloon can also be made of a different material that signals the user that the inner balloon is fully occluding the target vessel based on the pressure limit. The outer balloon does not have to be attached to the main single integral structure; it could also be attached in series to the single integral balloon unit, for instance attached to the tuohy-borst attachment. A variety of methods can be used to signal the user that the balloon has enough pressure to occlude the target vessel. An example of this, but not limited to this example, is that the balloon is made of a material that changes colour once the limit has been reached. Sensors could also be used to more precisely signal when the limit has been reached.

Figure 11:
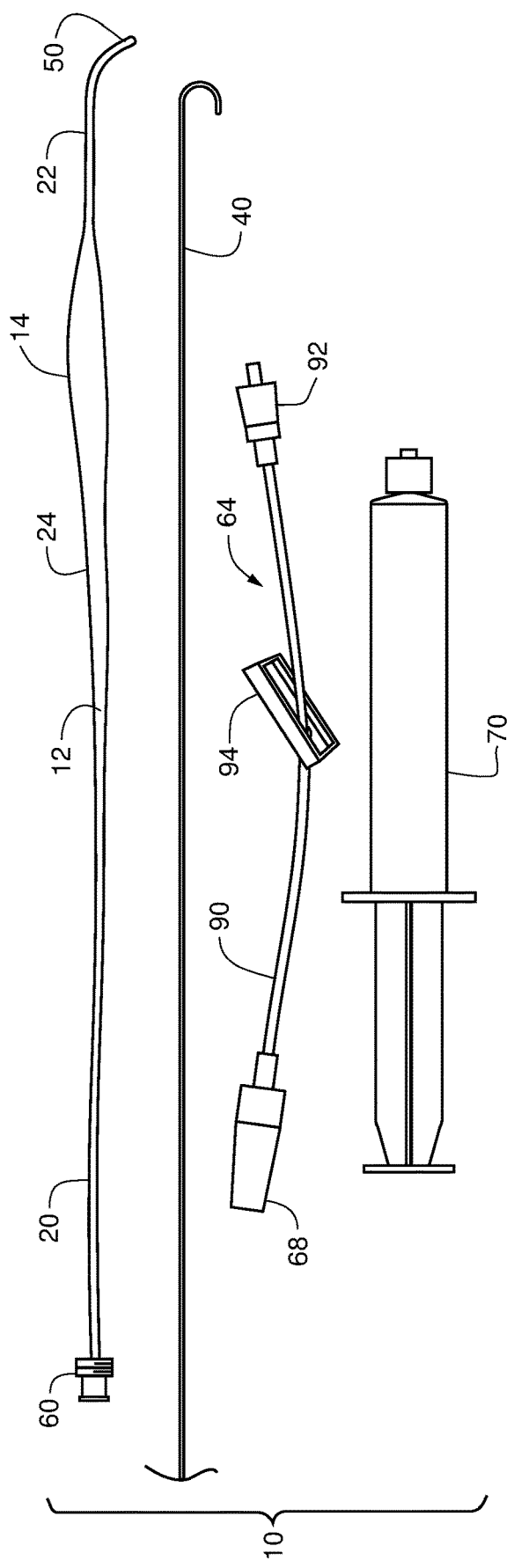
FIG. 11 is a top down component view of the occlusion device having an alternative handle assembly to that shown in FIGS. 8 and 9.

In another embodiment of the occlusion assembly 10, an example of which is shown in FIG. 11, the occlusion assembly 10 comprises an atraumatic stiff 0.035 inch PTFE-coated wire 40 with an atraumatic distal J-tip 42 that sits inside a blind-ended (see distal end region 50) compliant balloon shaft 12 that consists of a proximal neck portion 20, a distal neck portion 22 an expandable balloon portion 14 positioned therebetween and a leak proof luer lock 60 positioned at the proximal most end of the proximal neck portion 20.

A handle assembly 64 is provided for coupling to the luer lock 60. In the embodiment shown, the handle assembly 64 is provided as a more streamlined (and minimal packaging friendly) configuration than those of previous embodiments. Here, the handle assembly 64 is a piece of extension tubing 90 which includes one or more adapters 92 to engage the luer lock 60 and provide an inflation port 68 that is in fluid engagement of the lumen 24.

Retained on the extension tubing 90 is a locking tab 94. The locking tab 94 is loose on the extension tubing and is used to fix the wire on the extension tubing when the shaft 12 is being inserted or removed. Once the shaft 12 is in place and the tab 94 is engaged to fix the wire 40, the tab can be also be used to suture the shaft 12 to the patient's skin. The tab 94 may be disengaged when inflation of the balloon portion 14 commences (via coupling the syringe 70 to the inflation port 68 and injecting inflation fluid into the lumen 24).

The distal end region 50 of the balloon shaft 12 has a stiffer 1 cm bonded tip that facilitates the introduction into an introducer sheath hemostasis valve or equivalent 14 gauge angiocatheter.

In some embodiments there will be present a lanyard attachment or eye at the proximal end of the balloon shaft or assembly which allows a portion of the shaft 12 to be sutured to the skin once the balloon portion 14 is in its target location and inflated. This is to prevent slippage.

In another embodiment, in order to allow for partial-REBOA, a suture material (or wire) can be attached to the distal neck just distal to the expanded balloon portion which would travel parallel to the REBOA device and outside the body. This configuration allows for a standard angioplasty balloon to be threaded over the suture or wire up the expanded balloon portion 14. Once both balloons (balloon portion 14 of the present assembly 10 and that of the angioplasty catheter (not shown)) are inflated, a channel with gutters is created that allows some blood flow to proceed distally so that partial-REBOA is accomplished.

In one embodiment of a double balloon occlusion assembly, one balloon can be placed at the aortic bifurcation (zone 3) and another balloon in the descending thoracic aorta (zone 1). An advantage of this configuration over existing balloons (for example, Prytime's ER-REBOA) is that the balloon at the aortic bifurcation (especially when shaped like an ice cream cone) will anchor the whole device in place so that it doesn't slip out of the artery. In one embodiment, the balloon at the bifurcation is "ice cream cone" shaped and the balloon in the thoracic aorta is a spherical balloon. Optionally a long distal and/or proximal neck may be provided for the wire to fit into.

Other potential applications of the occlusion assembly 10, besides being used in REBOA, include but not limited to, being used as an intra-aortic balloon pump or as an embolization device by using the wire or some other method to detach the inflated balloon in an area that requires embolization. This balloon can also be used as an angioplasty balloon to dilate narrowed blood vessels, with the advantage of being extremely low profile.

In some embodiments, such as those intended for military applications, the various components can be made of a material that can be seen in the dark or that light up in low-light conditions.

EXAMPLES

Example 1—Single Balloon Occlusion Assembly

In the FIG. 2-5 example shown above, the occlusion assembly 10 has proximal and distal neck portions 20 and 22 and inflatable balloon portion 14 provided as a single integral piece made of low durometer urethane. The balloon portion 14 is inflatable to about 3-4 cm in diameter. The balloon is "ice-cream cone" shaped measuring 6 cm in length, with a 20 cm proximal neck and a 15 cm distal neck, having total length of 41 cm. The distal neck has a bond tip of 1 cm in length. A 30 cm amplatzer wire 40 with 0.035-inch diameter, with hydrophilic coating, and a J-tip is used (see FIG. 5). The inner lumen 24 has a diameter slightly greater than 0.035 inches and the distal and proximal neck portions 22 and 20 have an outer diameter of 55 mils. The fully inflated diameter of the balloon portion 14 is 4 cm. A handle assembly 64 equipped with a tuohy-borst valve 62 is attached to the proximal end of the balloon shaft 12.

Example 2—Double Balloon Occlusion Assembly

One example of a double balloon occlusion assembly has 20 cm proximal neck, 6 cm proximal ice cream cone balloon (inflated diameter of 3-4 cm), 25-30 cm middle neck, 3 cm distal spherical balloon (inflated diameter of diameter 3-4 cm), and 15 cm distal neck.

Example 3—Occlusion Device Kit

As shown in FIG. 9, the occlusion assembly 10 according to the present invention may be provided as a kit. The kit includes a 60 cc syringe 70, where the barrel that acts as a container for the balloon shaft 12 and connection pieces, as well as a sheath and angiocatheter 80. Optionally, the contents of the barrel are sterilized and are kept sterile by maintaining a closed space with the plunger.

Example 4—REBOA Procedure Using an Occlusion Assembly

1. Prepare a REBOA occlusion assembly 10. If not prepositioned within the shaft 12, thread the endovascular wire 40 through the balloon shaft 12 and into the blind ended tip 50. Preferably, the wire 40 will be pre-threaded within the lumen 24. The balloon portion 14 can be inflated to look for leaks and to facilitate the wire-threading. Once the wire is in place within the balloon shaft 12, a combination tuohy-borst/stop-cock combination is attached to the luer lock 60 to lock the wire 40 in place. A syringe 70 is attached and all of the air/fluid/gas is sucked out of the balloon to obtain extremely low profile.

Figure 10:
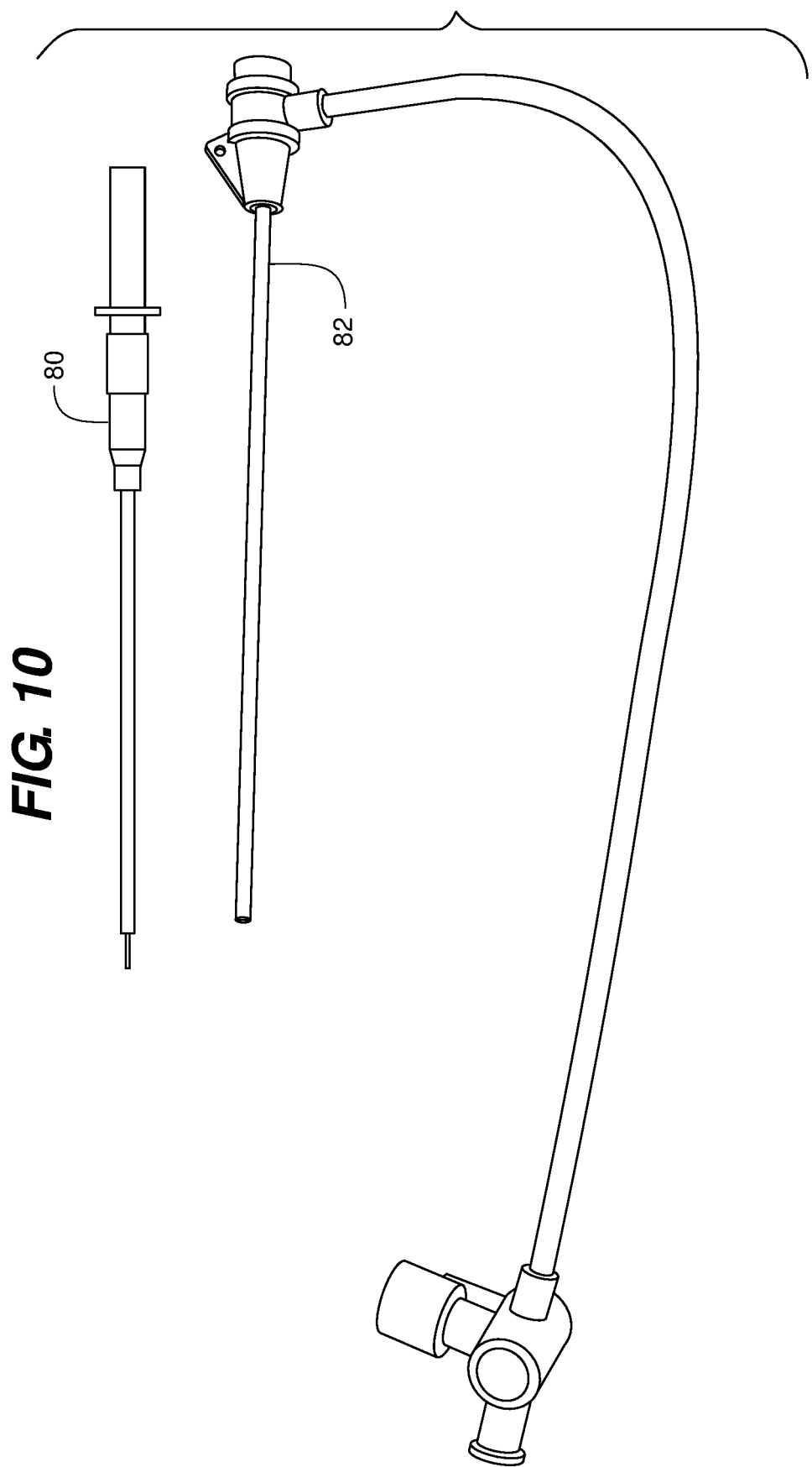
FIG. 10 is a perspective view of example types of devices through which the balloon shaft of the embodiments shown in FIGS. 1-9 are inserted, in order to pass into a blood vessel.

2. Percutaneous access is obtained. This is performed either by inserting a sheath 82 in a standard fashion or by using a syringe and angiocatheter with needle 80 to puncture the artery and get flashback of blood. An example angiocatheter with needle 80, as well as an example sheath 82 is shown in FIG. 10. For example, a 4 French sheath or a 14-gauge angiocatheter is used. The advantage of using a sheath 82 is that the one-way valve prevents blood loss. The disadvantage is that it takes longer to place this and requires more skill. The advantage of the angiocatheter 80 is the speed at which it can be obtained but disadvantage is that there can be blood loss. Ideally, there would be a valve on a 14 gauge angiocatheter (with needle) to prevent blood loss.

3. Insert the balloon shaft 12. The distal end of the shaft 12 is advanced into the sheath 82 or angiocatheter 80 to the appropriate length to occlude the aorta in the desired zone (see FIG. 1).

4. Inflate the device: With compliant balloons, a certain volume of fluid is used to inflate the balloon portion 14. For example, 10 cc of fluid is injected to inflate the balloon. Also, an arterial line can be placed in the other femoral artery or radial artery to indicate when aorta has been occluded and therefore no flow is detected (femoral arterial line) or blood pressure increases (radial arterial line).

5. Deflate the balloon portion 14 and remove the occlusion assembly 10 once bleeding is controlled.

6. Remove the sheath/angiocatheter 82/80 and apply pressure on the femoral vessel to achieve hemostasis.

The many features and advantages of the invention are apparent from the above description. Numerous modifications and variations will readily occur to those skilled in the art. Since such modifications are possible, the invention is not to be limited to the exact construction and operation illustrated and described.

What is claimed is:

1. A kit for occluding blood vessels, the kit comprising:
   a syringe for injection of a fluid, the syringe having a barrel;
   within the barrel is contained:
      an elongated shaft defining a single lumen therein and consisting of an inflatable balloon portion having a distal and a proximal end, a distal neck portion attached to the distal end of the inflatable balloon portion, and a proximal neck portion attached to the proximal end of the inflatable balloon portion;
      the single lumen extending through at least the proximal neck portion and the inflatable balloon portion, the single lumen constructed and arranged to act as a flow channel for passage of the fluid from the proximal neck portion to the inflatable balloon portion and to contain a wire;
   the wire; and
   at least one connection piece, the at least one connection piece being selected from the group consisting of a luer lock, at least one valve, at least one stop-cock, joiners, tuohy-borst attachment, and any combination thereof the at least one connection piece connects the elongated shaft to the syringe.

2. The kit according to claim 1, further comprising a sheath for insertion of the elongated shaft and wire into a blood vessel, the sheath placed inside the barrel.

3. The kit according to claim 1, wherein the barrel of the syringe is sterilized.

* * * * *